United States Patent
Oreste et al.

(10) Patent No.: US 6,992,183 B2
(45) Date of Patent: Jan. 31, 2006

(54) HIGHLY SULFATED DERIVATIVES OF K5 POLYSACCHARIDE AND THEIR PREPARATION

(76) Inventors: Pasqua Oreste, Via Mac Mahon, Milano (IT) 1-20155; Giorgio Zoppetti, Via Mac Mahon, 43, Milano (IT) 1-20155

(*) Notice: Subject to any disclaimer, the term of this patent is extended or adjusted under 35 U.S.C. 154(b) by 0 days.

(21) Appl. No.: 10/469,037

(22) PCT Filed: Feb. 26, 2002

(86) PCT No.: PCT/IB02/00561

§ 371 (c)(1),
(2), (4) Date: Aug. 26, 2003

(87) PCT Pub. No.: WO02/068477

PCT Pub. Date: Sep. 6, 2002

(65) Prior Publication Data

US 2004/0077848 A1    Apr. 22, 2004

(30) Foreign Application Priority Data

Feb. 27, 2001  (IT)  .......................... MI2001A0397

(51) Int. Cl.
*C07H 1/00* (2006.01)
*A61K 31/737* (2006.01)
(52) U.S. Cl. .................... 536/123.1; 536/124; 536/53; 536/54; 536/55.1; 536/55.2; 514/53; 514/54
(58) Field of Classification Search .................. 536/53, 536/54, 55.1, 55.2, 123.1, 124; 514/53, 54
See application file for complete search history.

(56) References Cited

U.S. PATENT DOCUMENTS 6,329,351 B1 * 12/2001 Naggi et al. .................. 514/56

FOREIGN PATENT DOCUMENTS

| WO | WO 92/17507 | 10/1992 |
|----|-------------|---------|
| WO | WO 97/43317 | * 11/1997 |
| WO | WO 98/34958 | 8/1998 |
| WO | WO 98/42754 | * 10/1998 |
| WO | WO 01/02597 | 1/2001 |

OTHER PUBLICATIONS

Manzoni et al, Journal of Bioactive and Compatible Polymers, 1993, vol. 8, 251-257.*
Manzoni et al, Journal of Bioactive and Compatible Polymers, 1993, 8, 251-257.*
Manzoni et al., "Extracelular K5 Polysaccharide of *Escherichia Coli*: Production and Characterization," Journal of Bioactive and Compatible Polymers, Lancaster, PA, vol. 8, No. 3, Jul. 1993, pp. 251-257.

* cited by examiner

*Primary Examiner*—James O. Wilson
*Assistant Examiner*—Ganapathy Krishnan
(74) *Attorney, Agent, or Firm*—Nixon & Vanderhye P.C.

(57) ABSTRACT

The purification of the *E.coli* K5 polysaccharide by treatment with isopropyl alcohol and elimination of lipophilic substances is described. The purified product can be used to prepare, after N-deacetylation, new N,O-sulfated polysaccharides with high degree of sulfation.

27 Claims, 2 Drawing Sheets

HIGHLY SULFATED DERIVATIVES OF K5 POLYSACCHARIDE AND THEIR PREPARATION

SUMMARY

The purification of the *E.coli* K5 polysaccharide by treatment with isopropyl alcohol and elimination of lipophilic substances is described. The purified product can be used to prepare, after N-deacetylation, new N,O-sulfated polysaccharides with high degree of sulfation.

BACKGROUND OF THE INVENTION

It is known that the capsular polysaccharide K5 isolated from a *E.coli* strain (herein below simply called "K5") described by W. F. Vann et al. (1981) in Eur. J. Biochem. 116, 359–364, shows the same sequence as the biosynthetic precursor of heparin and heparan sulfate (N-acetylheparosan) and is chemically constituted by repetitive disaccharide units formed by D-glucuronic acid and N-acetylglucosamine linked α1–4, while the disaccharide units d-glucuronyl-N-acetylglucosamine are linked β 1–4. The only difference, which is not important for the biological activities of the K5 and its derivatives, between the heparin precursor N-acetyl-heparosan and K5 polysaccharide, is the presence of a double bond in position 4(5) at the non reducing end of some chains of the polymer, as for instance described in EP 489647 and EP 544592 herein below mentioned.

After this first publication, other papers and patent applications described the preparation of the *E.coli* K5 polysaccharide having molecular weight ranges from few thousand to many hundred thousand Daltons. For example EP 333243, IT 1230785, EP 489647, EP 544592, WO 92/17507, WO 102597, and the paper of M. Manzoni et al. (1996), Journal Bioactive Compatible Polymers, 11, 301–311 are indicated.

DESCRIPTION OF THE PRIOR ART

According to the literature, the K5 from fermentation of *E.coli* strains was purified to eliminate for example nucleic acids, endotoxins, pyrogens or in general proteins by various methodologies.

Thus, for example, W. F. Vann et al. (1981) purified the K5, isolated for the first time, after precipitation with quaternary ammonium salts, using three precipitations with 80% ethanol. In EP 333243, the purification is performed by precipitation with a quaternary ammonium salt, extraction and isolation of the K5. In EP 489647 and EP 544598, the K5 is purified by precipitation with ethanol and exclusion and/or ionic exchange chromatography. According to WO 92/17507, the purification is performed by precipitation with ethanol, dialysis and, after centrifugation of the dialyzed solution and elimination of the solid, freeze-drying of the resulting solution. According to M. Manzoni et al. (1996) and to WO 01/02597, that describe a procedure for the preparation of K5 by fermentation in a culture medium containing defatted soy, salts and glucose, the purification of K5 is performed using 1M NaCl solution, ultrafiltration and ionic exchange chromatography of a solution containing K5 obtained by ethanol precipitation.

Furthermore, K5 from fermentation was chemically modified to obtain heparin-like products. Thus, among the above mentioned documents, WO 92/17507, EP 489647 and EP 544592 describe N,O-sulfated K5 with low and high molecular weight having anticoagulant and antithrombotic activities, IT 1230785 and WO 92/17507 describe N-deacetylated-N,O-sulfated derivatives of K5 having a certain number of glucuronic units epimerized to iduronic units, WO 98/09636 describes N-deacetylated-N,O-sulfated K5 having antimetastatic activity.

Finally, for the O-sulfation of N-sulfate K5, literature teaches how to modulate the number of sulfate groups that can be introduced on the hydroxy groups of the disaccharide unit. Particularly, Casu et al. (1994) Carbohydrate Research, 263, 271–284 describe the N-deacetylation of K5, the N-sulfation and three methods of O-sulfation indicated as B, C and AC. According to method C, in which the sulfation of the N-sulfate K5 is performed using 10 mole equivalents of sulfating agent per free hydroxyl group at a temperature of 25–55° C. for a period of time ranging from 1 to 24 hours, polysulfated compounds are obtained after a further N-sulfation having a maximum sulfate/carboxyl ratio of 3.1 that herein below will be indicated as N,O-oversulfated K5.

The other K5 derivatives described herein below are also designated as follow: "N-deacetylated K5" the N-deacetylated K5 polysaccharide, "N-sulfate K5" the N-deacetylated-N-sulfated K5 polysaccharide, "N,O-sulfate K5" the N-deacetylated-N,O-sulfated K5 polysaccharide and "N,O-oversulfated K5" the N-deacetylated-N,O-sulfated K5 polysaccharide with high degree of sulfation, for example obtained according to the above mentioned Method C described by Casu et al. (1994).

SUMMARY OF THE INVENTION

Performing the O-sulfation of the N-sulfate K5 according to the Method C it was observed that while in the case of heparin-like compounds (i.e. having a certain percentage of uronic units as iduronic acid) and in the case of K5 it is possible to achieve a high degree of sulfation, in the case of N-sulfate K5 the N,O-oversulfated K5 obtained showed a degree of sulfation which did not reach 3.2 sulfate groups per disaccharide unit. This evidence explains the lacking of literature reference to N,O-oversulfated K5 having more than 3.2 sulfate groups per disaccharide unit, products potentially interesting for their high anionic degree.

It was now been found that by purifying the K5 obtained by fermentation by treatment with isopropanol in a highly saline solution, a pure K5 polysaccharide is obtained, practically free of lipophilic substances.

Moreover it was found that by submitting the K5 free of lipophilic substances thus obtained to a N-deacetylation, to a N-sulfation, to a O-sulfation according to the Method C and, optionally, to another N-sulfation, new N,O-oversulfated K5 compounds having a sulfation degree higher than 3.2 and in general equal to or higher than 3.5 are obtained.

DETAILED DESCRIPTION OF THE INVENTION

Figure 1:
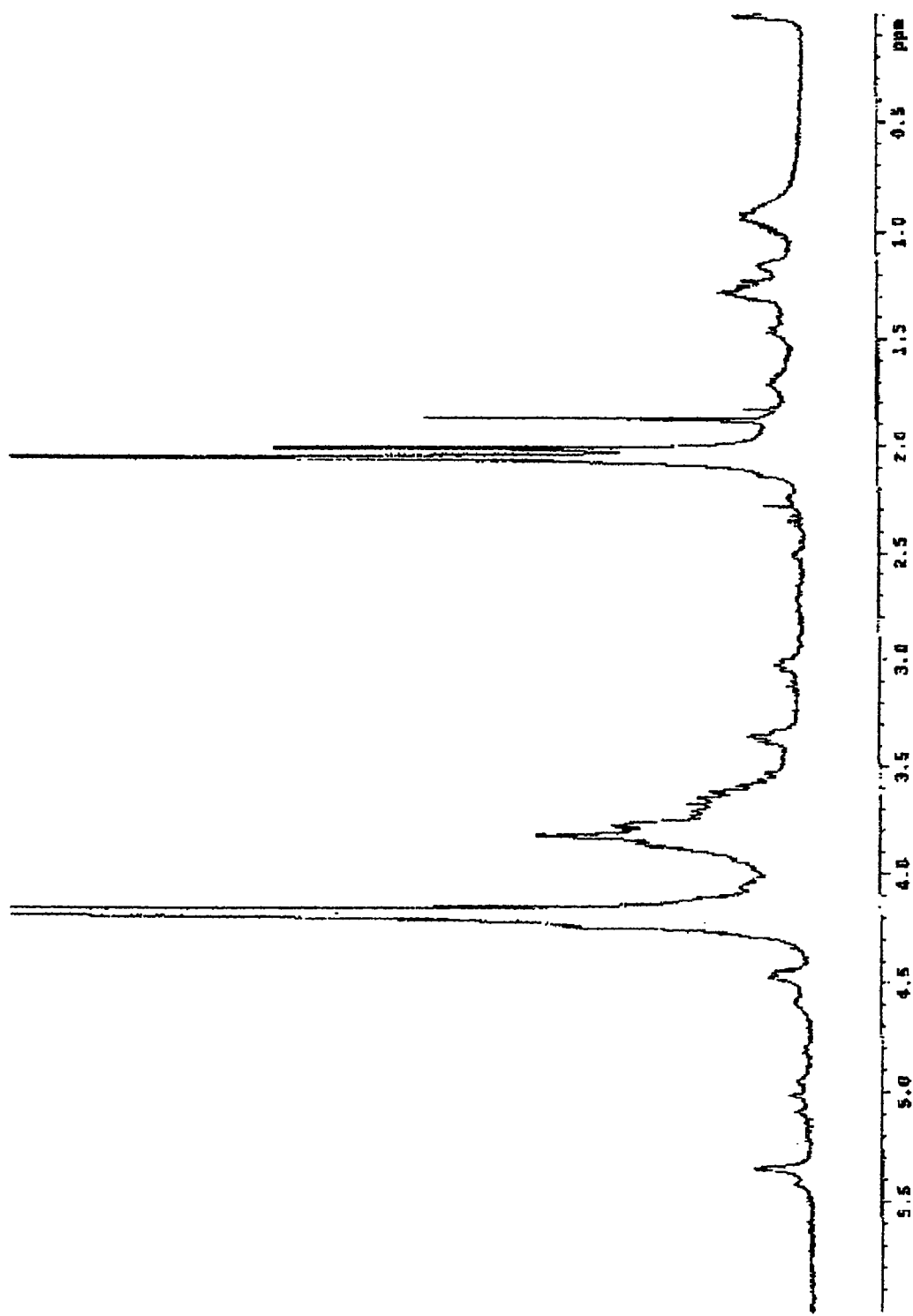
FIG. 1 shows the $^1$H-NMR spectrum of K5 obtained from fermentation with a 80% purity.

Thus, according to one of its aspects, the present invention provides a process for the preparation of new N,O-oversulfated K5 having a sulfation degree higher than 3.2 which comprises (a) treating a K5 obtained from fermentation with isopropanol in a highly saline aqueous solution;
(b) submitting the thus purified K5 to a N-deacetylation by alkaline hydrolysis and to a subsequent N-sulfation by treatment with a N-sulfating agent;
(c) treating the ammonium salt of the N-sulfate K5 thus obtained with an O-sulfating agent under the O-oversulfation conditions; and
(d) if required, submitting the compound thus obtained to a N-resulfation and isolating N,O-oversulfated K5 as sodium salt, which is optionally converted to another salt.

The term "sulfation degree" designates the number of sulfate groups per disaccharide unit, expressed as sulfate/carboxyl ratio.

The term O-oversulfation means the oversulfation of the N-sulfate K5, obtained for example by using the Method C.

In step (a), the K5 used as starting material can be one of the products obtained by fermentation of wild or cloned *Escherichia Coli* strains producing K5. In particular the K5 described in literature like those above cited can be used, advantageously those described by M. Manzoni et al. Journal Bioactive Compatible Polymers 1996, 11, 301–311 and the one illustrated in PREPARATION I herein below.

More advantageously, the K5 starting material has a low molecular weight, in particular with a distribution of from about 1,500 to about 15,000, preferably from about 2,000 to about 9,000, with a mean molecular weight of about 5,000, or a higher molecular weight, in particular with a distribution of from about 10,000 to about 50,000, preferably from about 20,000 to about 40,000 and a mean molecular weight of about 30,000. Preferably the K5 starting material has a molecular weight distribution of from about 1,500 to about 50,000, with a mean molecular weight of 20,000–25,000.

The molecular weight of K5 and of its derivatives here described is intended calculated using fractions of heparin with known molecular weight as standards; all the molecular weights in the present invention are expressed in Dalton.

The starting material can be a previously purified K5 from which, for example, the endotoxins, the pyrogens o other impurities have been eliminated with known methodologies.

Likely, if the K5 obtained at the end of passage (a) is used for pharmaceutic purposes or for the preparation of N,O-sulfate K5 for pharmaceutical use, it can be purified from pyrogens and endotoxins.

Practically, the K5 starting material is dissolved in a 2–5 M solution, preferably of sodium chloride, at a concentration of from 0.5 to 10% and treated with 1–3 volumes of isopropanol at a temperature of 0–8° C. and the thus obtained solution, brought to 2–4 M by the further addition of salt, preferably sodium chloride.

After 1–18 hours at the same temperature, the product of step (a) completely precipitates and is isolated by filtration or centrifugation. If the purity of the product is not satisfactory, the procedure of step (a) is repeated. The solid product thus obtained is redissolved in water and recovered by ultrafiltration with a membrane.

At the end of step (a) a K5 having the same characteristics as those of the starting material, but being substantially free of lipophilic substances is obtained.

Practically, the K5 free of lipophilic substances is obtainable by a process which comprises (a1) treating a K5 from fermentation, dissolved in a 4 M solution of sodium chloride at 4° C. with 1 volume of isopropanol, (a2) bringing the saline solution to 3 M by adding the calculated amount of a sodium chloride saturated solution, (a3) keeping the solution at 4° C. overnight and (a4) isolating the product by centrifugation and eliminating the salts by ultrafiltration.

By the purification with isopropanol it is thus possible to obtain a K5 free of lipophilic substances which has a purity higher than 99%. This K5 allows to obtain a high O-sulfation in the next step (c).

In step (b), the N-deacetylation is performed according to the known methods of alkaline hydrolysis, for example with hydrazine sulfate in hydrazine or with a base such as an alkaline hydroxide, for example sodium or potassium hydroxide, in water. Preferably the reaction is performed in an aqueous solution of sodium hydroxide at a temperature of 40–80° C., by controlling the course of the reaction. In general, after at most 30 hours, but practically after 12–24 hours the N-deacetylation is complete and the alkalinity of the medium is neutralized by treatment with an acid, preferably hydrochloric acid.

The solution containing the K5 and the salts is subsequently treated with a N-sulfating agent such as the adduct of a tertiary organic base with sulfuric anhydride (sulfur trioxide), such as pyridine.sulfur trioxide ($C_5H_5N.SO_3$) or a trialkylamine.sulfur trioxide such as trimethylamine.sulfur trioxide in the presence of an alkaline carbonate such as sodium carbonate. The reaction can be performed at room temperature (20–30° C.), but it is also possible to work at higher temperatures (up to about 65° C.) to shorten the reaction time. The addition of the alkaline carbonate and of the sulfating agent can be performed concurrently or the alkaline carbonate is introduced in bulk and the sulfating agent is added subsequently, stepwise, in a period of time which can last from 5 minutes to 12 hours. At the end of the reaction the mixture, at room temperature, is brought to pH 7.5–8 by an acid, preferably hydrochloric acid and the salts are eliminated for example by diafiltration. The so obtained solution, containing the N-sulfate K5 as an alkaline salt, can be passed to the subsequent step (c), or it can be concentrated and the N-sulfate K5 can be isolated as sodium salt with conventional methods. The thus obtained N-sulfate K5 is 90–100% sulfated.

In step (c) a solution containing the alkaline N-sulfate K5 obtained in step (b) is neutralized for example by passage on a cationic exchange resin, like IR 120 H$^+$ till acid pH. The acidic solution so obtained is treated with a tertiary or quaternary organic base, for example with a trialkylamine like tributylamine, or with the hydroxide of a tetraalkylammonium, preferably tetrabutylammonium hydroxide, reduced to the minimum volume and freeze dried. The thus isolated ammonium salt of the N-sulfate K5 is suspended in a polar aprotic solvent such as dimethylformamide or dimethylsulfoxide and treated with an O-sulfating agent, for example with the adduct $C_5H_5N.SO_3$. The adduct $C_5H_5N.SO_3$ can be used either in the solid state or in solution in the same polar aprotic solvent. The sulfation is performed at a temperature that can vary from the room temperature (20–30° C.) to 70° C., preferably from 40 to 60° C., for a period of time of from 2 to 24 hours.

At the end of the reaction, the solution at room temperature is treated with sodium chloride saturated acetone till complete precipitation. The precipitate is separated from the solvent by filtration, dissolved in the minimum amount of deionized water, for example 100 ml, and sodium chloride is added to the solution till a 0.2 M concentration. The solution is brought to pH 7.5–8 with 2N sodium hydroxide and treated with acetone till complete precipitation. After filtration the solid is dissolved in 100 ml of deionized water and purified from the residual salts by ultrafiltration as described in step (b).

If from the analysis by $^{13}$C-NMR of a lyophilized sample of the thus obtained product a partial N-desulfation occurred during the oversulfation, the product is submitted to step (d).

In step (d) the product obtained at the end of step (c) is treated with a N-sulfating agent by operating under the conditions of step (b) till complete N-sulfation, repeating the procedure if the N-sulfation is not complete.

The N,O-oversulfated K5 thus obtained is isolated as sodium salt, that can be transformed into another salt, like potassium, calcium, magnesium, aluminum, zinc or complex salts using known methods, for example by ionic exchange with a suitable resin, by precipitation with solvents or by ultrafiltration with membranes.

According to another of its aspects, the present invention provides a pure K5 from fermentation, substantially free of lipophilic substances.

The purity of the new purified K5 from fermentation can be assayed by $^1$H-NMR spectrum, by UV spectrum, by carbazole reaction or by a kit for the protein determination. By these assays it was demonstrated that the K5 obtained at the end of step (a) has, as the essential characteristic, a $^1$H-NMR spectrum in which signals in the field below 1.5 ppm are absent. Moreover the nucleic acids are not detectable, (absorbance 0 at 260 nm with a standard UV spectrophotometer) and the proteins are not higher than 0.5%, advantageously below 0.25%, more advantageously below 0.1%, preferably below 0.03% according to BioRad kit.

Actually, the new pure K5 obtained at the end of step (a) is free from lipophilic substances and nucleic acids. The use of "substantially", referred to the absence of lipophilic substances and of "not detectable" referred to the nucleic acids takes in account the sensitivity of the instruments used which have not revealed the presence of the above mentioned impurities.

Thus it was established that the $^1$H-NMR spectrum of the pure K5 polysaccharide obtained in this way lacks the signals at <1.5 ppm characteristics of the methyl group of lipophilic substances.

The new thus purified K5 compounds, which allow the preparation of N,O-oversulfated K5 with a high degree of sulfation have preferably a low molecular weight, in particular with a distribution of from about 1,500 to about 15,000, preferably from about 2,000 to about 9,000, with a mean molecular weight of about 5,000, or a higher molecular weight, in particular with a distribution of from about 10,000 to about 50,000, preferably from about 20,000 to about 40,000 with a mean molecular weight of about 30,000. Preferably the K5 starting material has a molecular weight distribution of from about 1,500 to about 50,000 with a mean molecular weight of 20,000–25,000.

Thus, according to another of its aspects, the present invention provides new N,O-oversulfated K5 compounds having a degree of sulfation higher than 3.2 and their salts. Advantageously the new N,O-oversulfated K5 polysaccharides have a degree of sulfation of from 3.2 to 4, more advantageously from 3.5 to 4, preferably from 3.7 to 4. Preferably the salts of the new N,O-oversulfated K5 are pharmaceutically acceptable.

Advantageously said N,O-oversulfated K5 have a low molecular weight, in particular with a distribution of from about 2,000 to about 16,000, preferably from about 2,500 to about 10,000 with a mean molecular weight of about 6,500, or a somewhat higher molecular weight, in particular with a distribution of from about 13,000 to about 65,000, preferably from about 25,000 to about 50,000 with a mean molecular weight of about 40,000. Preferably the N,O-oversulfated K5 of the present invention has a molecular weight distribution of from about 2,000 to about 65,000, with a mean molecular weight of 25,000–30,000. Also N,O-oversulfated K5 compounds having a very low mean molecular weight, for example of from about 2,000 to 5,000, obtained by depolymerization, constitute very interesting products.

The depolymerization that allows the preparation of the N,O-oversulfated K5 of mean molecular weight of from 2,000 to 5,000 can be performed at the end of one of steps (b)–(d) of the process illustrated above, preferably at the end of step (b) or on the final N,O-oversulfated K5.

The depolymerization can be performed according to one of the known methods for the depolymerization of heparin, for example by nitrous acid and subsequent reduction with sodium borohydride (EP 37319), by periodate (EP 287477), by free radicals (EP 121067) or by β-elimination (EP 40144). According to a preferred embodiment, the depolymerization is performed on a N-sulfate K5 obtained at the end of step (b) with nitrous acid and subsequent reduction with sodium borohydride as detailed in EP 544592. At the end of the depolymerization and reduction, the low molecular weight product thus obtained is submitted to steps (c) and, optionally, (d) and the N,O-oversulfated K5 is isolated.

Alternatively, the same process of depolymerization and reduction can be applied to a N,O-oversulfate K5 with high molecular weight and the corresponding low molecular weight product is obtained straightforwardly.

Among the salts of the above mentioned N,O-oversulfated K5 compounds, the sodium, potassium, calcium, magnesium aluminum and zinc salts are preferred.

According to a further aspect, the present invention provides novel N,O-oversulfated K5 polysaccharides having a degree of sulfation higher than 3.2, in particular from 3.2 to 4, advantageously from 3.5 to 4, preferably from 3.7 to 4, obtainable by a process which comprises (a) treating a K5 from fermentation with isopropanol in a highly saline solution;

(b) submitting the thus obtained K5 to a N-deacetylation by alkaline hydrolysis and to a subsequent N-sulfation by treatment with a N-sulfating agent;

(c) treating an ammonium salt of the N-sulfate K5 thus obtained with an O-sulfating agent in the O-oversulfation conditions;

(d) if needed, submitting the product thus obtained to a N-sulfation and isolating the N,O-oversulfated K5 as sodium salt which, if necessary, is converted into another salt.

The N,O-oversulfated K5 obtainable by the above mentioned process have a degree of sulfation of from 3.2 to 4, advantageously from 3.5 to 4, preferably from 3.7 to 4. The new N,O-oversulfated K5 compounds obtained according to the process of the present invention, especially as salts thereof, are highly anionic products useful in the cosmetic industry as co adjuvant against the loss of hairs and in the pharmaceutical industry as products able to catch the free radicals.

Said N,O-oversulfated K5 compounds are completely sulfated in the positions 6-O- and 2-NH- of the glucosamine units whilst in the glucuronic units they are 2,3-O-disulfated or (2-O- or 3-O)monosulfated, the percent of the sulfate groups in the glucuronic units depending upon the sulfation degree.

Thus, it is a further object of the invention to provide novel N,O-oversulfated K5 constituted by a mixture of chains in which at least 90% of said chains are represented by the following formula (I)

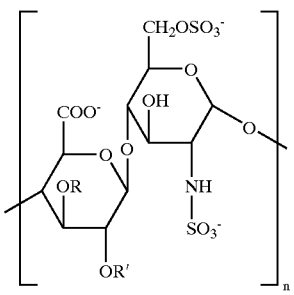

(I)

wherein n is 3 to 100 and R and R' are hydrogen or a $SO_3^-$ group, at least one of R and R' being other than hydrogen, with the proviso that one of R and R' is hydrogen and the other is $SO_3^-$ in from 0 to 40 % of the n units; the sulfation degree being from 3.2 to 4 and units; the sulfation degree being from 3,2 to 4 and the corresponding cation being a chemically or pharmaceutically acceptable one.

In this context, the expression "chemically acceptable" is referred to a cation which is useful for possible further syntheses, such as ammonium or ($C_1$–$C_4$)trialkylammonium ion, or for the purification of the product, preferred cations being the above-mentioned sodium, potassium, magnesium, aluminum and zinc ions. In the remaining up to 10% chains in said mixture of chains, for a given sulfation degree a certain amount of $SO_3^-$ groups of glucosamine units may have been splitted off from the 2-position and transferred onto the 3-OH group of said glucosamine units.

Their high anion content confers to the N,O-oversulfated K5 polysaccharides of the present invention a good activity against the free radicals. Due to their low toxicity they are useful active ingredients for the preparation of pharmaceutical and cosmetic compositions.

Thus, the present invention also provides pharmaceutical compositions containing, as an active ingredient thereof, a pharmacologically active amount of a N,O-oversulfated K5 having a sulfation degree higher than 3.2, advantageously from 3.2 to 4, more advantageously from 3.5 to 4, preferably from 3.7 to 4 or one of its pharmaceutically acceptable salts in admixture with a pharmaceutical excipient.

In the pharmaceutical compositions of the present invention for the oral, subcutaneous, intravenous, intramuscular, transdermic or topical administration, the active ingredients are preferably administered in dosage units, in admixture with the classic pharmaceutical carriers or vehicles.

The dosage can vary in function of the age, weight, and health conditions of the patient. This dosage includes the administration of a dose of from 1 to 1,000 mg, advantageously from 10 to 750 mg, preferably from 250 to 500 mg, from one to three times per day by intravenous, subcutaneous, oral, intramuscular, transdermic or topical route.

According to another of its aspects, the present inventions relates a cosmetic composition containing, as one of its active ingredients, a N,O-oversulfated K5 having a degree of sulfation higher than 3.2, advantageously from 3.2 to 4, more advantageously from 3.5 to 4, preferably from 3.7 to 4, or one of its pharmaceutical acceptable salts, in admixture with a cosmetic excipient.

A salt chosen among the group consisting in the sodium, potassium, calcium, magnesium, aluminum and zinc salts constitutes valid active ingredient of the compositions of the present invention.

Finally, according to a further aspect, the present invention also provides pharmaceutical and cosmetic compositions comprising the new purified K5 of the invention as an active ingredient.

PREPARATION I

Preparation of the K5 Polysaccharide from *Escherichia Coli*

First a fermentation in flask using the following medium is performed:

| | |
|---|---|
| Defatted soy | 2 g/l |
| $K_2HPO_4$ | 9.7 g/l |
| $KH_2PO_4$ | 2 g/l |
| $MgCl_2$ | 0.11 g/l |
| Sodium citrate | 0.5 g/l |
| Ammonium sulfate | 1 g/l |
| Glucose | 2 g/l |
| Water | 1,000 ml |
| pH = 7.3 | |

The medium is sterilized at 120 ° C. for 20 minutes. The glucose is prepared separately as a solution which is sterilized at 120° C. for 30 minutes and added to the medium under sterile conditions. The flask is inoculated with a suspension of *E.Coli* cells Bi 8337/41 (O10:K5:H4) from a slant maintained in Tryptic soy agar, and incubated at 37° C. for 24 hours under controlled stirring (160 rpm, 6 cm of run). The bacterial growth is measured counting the cells with a microscope. In a further step, a Chemap-Braun fermentor with a volume of 14 liters containing the same medium above is inoculated with the 0.1% of the above flask culture and the fermentation is performed with 1 vvm aeration (vvm=air volume for liquid volume for minute), 400 rpm stirring and temperature of 37° C. for 18 hours. During the fermentation pH, oxygen, residual glucose, produced K5 polysaccharide and bacterial growth are measured. At the end of the fermentation the temperature is raised to 80° C. for 10 minutes. The cells are separated from the medium by centrifugation at 10,000 rpm and the supernatant is ultrafiltrated through a SS316 (MST) module equipped with PES membranes with a nominal cut off of 800 and 10,000 D to reduce the volume to ⅕. Then K5 polysaccharide is precipitated adding 4 volumes of acetone at 4° C. and left to sediment for one night at 4° C. and finally is centrifuged at 10,000 rpm for 20 minutes or filtrated. Then a deproteinization using a protease of the type II from *Aspergillus orizae* in 0.1 M NaCl and 0.15 M ethylenediaminotetracetic acid (EDTA) at pH 8 containing 0.5% sodium dodecyl sulfate (SDS) (10 mg/l of filtrate) at 37° C. for 90 minutes is performed. The solution is ultrafiltrated on a SS 316 module with a nominal cut off membrane of 10,000 D with 2 extractions with 1M NaCl and washed with water until the absorbance disappears in the ultrafiltrate. K5 polysaccharide is then precipitated with acetone and a yield of 850 mg/l of fermentor is obtained. The purity of the polysaccharide is measured by uronic acid determination (carbazole method), proton and carbon NMR, UV and protein content. The purity is higher than 80%. The so obtained polysaccharide is composed of two fractions with different molecular weight, 30,000 and 5,000 D respectively as obtained from the HPLC determination using a 75 HR Pharmacia column and one single fraction with retention time of about 9 minutes using two columns of Bio-sil SEC 250 in series (BioRad) and $Na_2SO_4$ as mobile phase at room temperature and flow rate of 0.5 ml/minute. The determination is performed against a curve obtained with heparin fractions with known molecular weight.

The $^1$H-NMR of the purified K5 thus obtained is reported in FIG. 1.

As it is possible to note, in the region below 1.5 ppm a lot of signals attributable to the methyls of lipophilic substances are present.

EXAMPLE 1

K5 Purification

Figure 2:
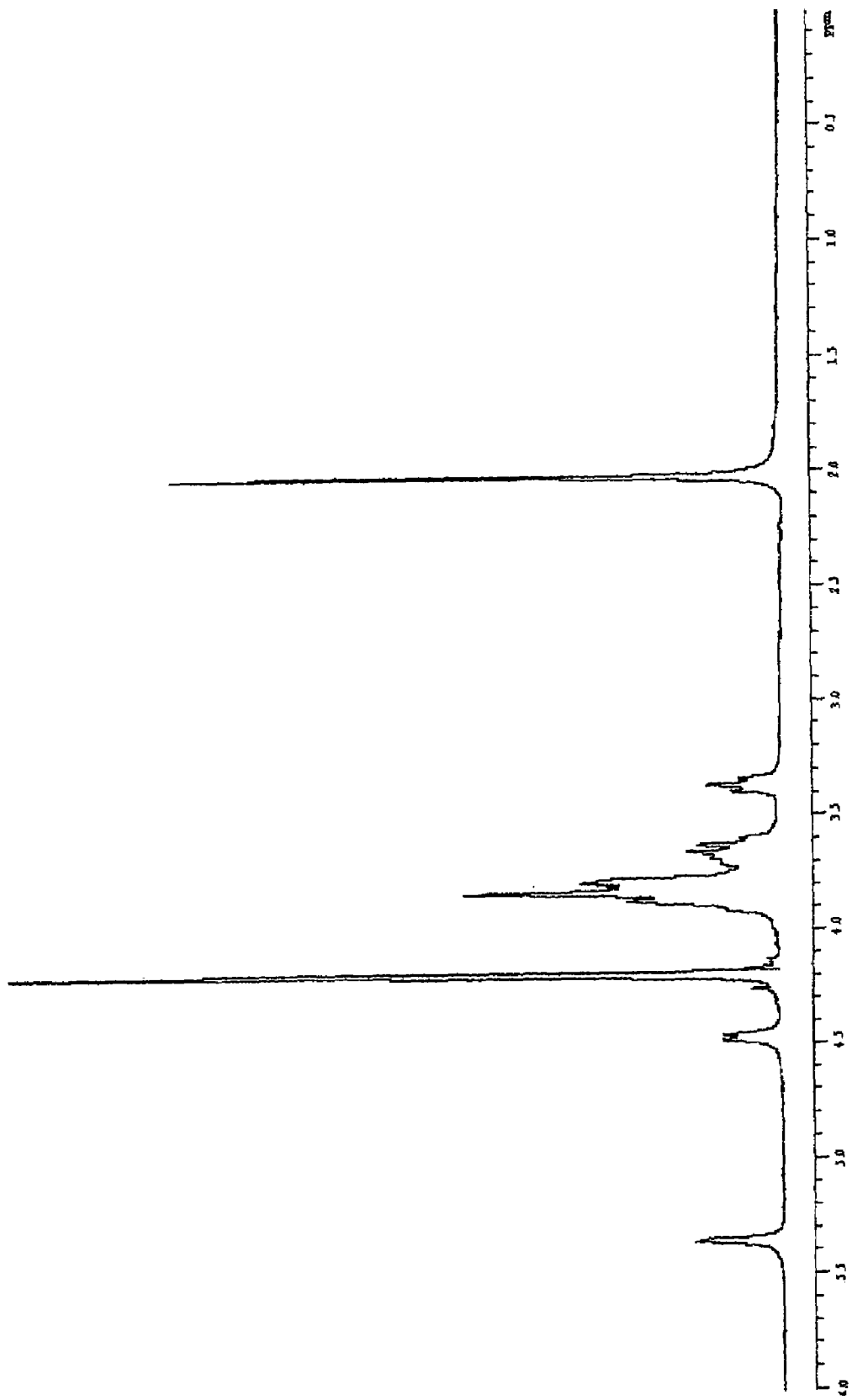
FIG. 2 shows the $^1$H-NMR spectrum of K5 obtained from fermentation free of lipophilic substances with a purity >99%.

In 100 ml of an aqueous solution containing 4M sodium chloride and thermostated at 4° C. are dissolved 5 gr of the K5 obtained at the end of PREPARATION I and 1 volume of cold isopropanol is added to the thus obtained solution. The salt concentration of the solution is brought to 3 M by adding a calculated amount of a saturated solution of sodium chloride and the cooled solution is kept at cold temperature (about 4° C.) overnight. The precipitate formed is separated by centrifugation at 10,000 rpm for 20 minutes and the purity of the product is controlled by dialysis for one night and subsequent $^1$H-NMR analysis from which signals in the region below 1.5 ppm must be absent. If necessary, the procedure of dissolution in water containing 4M NaCl and precipitation with isopropanol is repeated. The precipitate is dissolved in water and ultrafiltrated on a Miniplate membrane Millipore with a 10,000 D cut off till disappearance of the salts. A K5 having a purity of at least 99% and whose $^1$H-NMR spectrum is reported in FIG. 2 is obtained.

As it can be noted, in the region below 1.5 ppm there are no trace of lipophilic impurities.

The protein content calculated by using BioRad kit is 0.02% and the nucleic acids are not detectable (absorbance 0 at 260 nm).

EXAMPLE 2

Preparation of a N,O-oversulfated K5

(i) N-deacetylation

Ten grams of pure K5 polysaccharide prepared as described in Example 1 are dissolved with 1,000 ml of 2 N sodium hydroxide and the solution thus prepared is kept at 60° C. for 24 hours. The solution is brought to room temperature and then to neutral pH with 6N hydrochloric acid.

(ii) N-sulfation

To the solution containing the deacetylated K5, kept at 40° C., 16 g of sodium carbonate and subsequently, in 4 hours, 16 g of pyridine.sulfur trioxide are added. At the end of the reaction, after 24 hours, the solution is brought to room temperature and then to pH 7.5–8 with a 5% solution of hydrochloric acid. The product is purified from salts by diafiltration using a spiral membrane of 1,000 D (Prepscale Cartridge-Millipore). The process is ended when the conductivity of the permeate is below 1,000 $\mu$S, preferably below 100 $\mu$S. The intradialysis is reduced till a polysaccharide concentration of 10% using the same dialysis system in concentration. The concentrated solution is freeze dried. The analysis of the $^{13}$C-NMR does not show N-acetyl or $NH_2$ residual groups.

(iii) O-oversulfation

The freeze dried product obtained at the end of step (ii) is dissolved in 100 ml of deionized water and the solution is brought to 10° C. with a cooling bath then passed onto a cationic exchange resin IR120H$^+$ (100 ml). Both the column and the reservoir are kept at 10° C. After the passage of the solution containing the sample the resin is washed with deionized water till the pH of the permeate is higher than 6 (about 3 volumes of deionized water). The acidic solution is brought to neutrality (pH 7) with tetrabutylammonium hydroxide (15% aqueous solution), then reduced to the minimum volume and freeze dried. The tetrabutylammonium salt is dissolved in 400 ml of dimethylformamide and added with 35 g of $C_5H_5N.SO_3$ in solid form. The solution is kept at 50° C. for 24 hours. At the end of the reaction the solution is cooled to room temperature and added with 3 volumes of sodium chloride saturated acetone, cooled to 4° C. till complete precipitation (12 hours). The precipitate is separated from the solvent by filtration, solubilized with the minimum amount of deionized water (about 100 ml) and to the solution sodium chloride till 0.2 M concentration is added.

The solution is brought to pH 7.5–8 with 2N sodium hydroxide and treated with 2 volumes of acetone till complete precipitation. The precipitate is separated from the solvent by filtration. The solid obtained is solubilized with 100 ml of deionized water and purified from the residual salts by ultrafiltration as described in step (ii) using a spiral membrane of 1,000 D (Prepscale Cartridge Millipore).

(iv) N-sulfation

The solution thus obtained, containing the O-sulfated product, is treated as previously described in step (ii) for the N-sulfation. The product shows a mean molecular weight of 15,000 D and a sulfate/carboxyl ratio of 3.84. The distribution of the sulfate groups, determined by the $^{13}$C-NMR is the following: the glucosamine unit of the constitutive disaccharide is 100% N-sulfated and 6-O sulfated, while, as to the glucuronic units, 30% are monosulfated and 70% disulfated.

EXAMPLE 3

Preparation of a N,O-oversulfated K5

As starting material a K5 obtained and characterized as described by M. Manzoni et al. (1996) is used. The K5 thus prepared is purified as described in example 1 and a pure K5 in which the signals below 1.5 ppm are absent, free of nucleic acids and with a protein content of 0.5% is obtained. By operating as described in Example 2 a N,O-oversulfated K5 having mean molecular weight of 13,000 and a sulfate to carboxyl ratio of 3.54 is obtained.

What is claimed is:

1. A process for the preparation of N,O-oversulfated K5 polysaccharide having a sulfation degree higher then 3.2, which comprises
    (a) treating a K5 polysaccharide from fermentation with isopropanol in a 2–5M saline aqueous solution to purify the K5;
    (b) submitting the thus purified K5 polysaccharide to a N-deacetylation followed by a subsequent N-sulfation by treatment with an N-sulfating agent;

(c) treating an ammonium salt of the N-sulfate K5 polysaccharide thus obtained with an O-sulfating agent under O-oversulfation conditions; and (d) if necessary, submitting the product thus obtained to a N-sulfation and isolating the N,O oversulfated K5 polysaccharide.

2. The process of claim 1, wherein the starting K5 polysaccharide has a molecular weight with a distribution from about 1,500 to about 15,000 Da.

3. The process of claim 2, wherein said molecular weight distribution is from about 2,000 to about 9,000 Da with a mean molecular weight of about 50,000 Da.

4. The process of claim 1, wherein the starting K5 polysaccharide has a molecular weight with a distribution from about 10,000 to about 50,000.

5. The process of claim 4, wherein said molecular weight distribution is from about 20,000 to about 40,000 Da with a mean molecular weight of about 30,000 Da.

6. The process of claim 1, wherein the starting K5 polysaccharide has a molecular weight with a distribution from about 2,000 to about 50,000 Da with a mean molecular weight of 20,000–25,000 Da.

7. The process of claim 1, wherein, in step (b), the N-deacetylation by alkaline hydrolysis is carried out with sodium hydroxide.

8. The process of claim 1, wherein pyridine-sulfur trioxide or trimethylamine-sulfur trioxide adduct is used as N-sulfating agent.

9. The process of claim 1, wherein, in step (c), the tetrabutylammonium salt is used as an ammonium salt.

10. The process of claim 1, wherein, in step (c), pyridine-sulfur trioxide adduct is used as sulfating agent.

11. The process of claim 1, wherein the N,O-oversulfated K5 polysaccharide is isolated as sodium salt.

12. The process of claim 11, wherein said sodium salt is converted into another salt.

13. The process of claim 12, wherein said other salt is selected from the group consisting of potassium, calcium, magnesium, aluminum and zinc salts.

14. A N,O-oversulfated K5 polysaccharide having a sulfation degree higher than 3.2, or a salt thereof.

15. The N,O-oversulfated K5 polysaccharide of claim 14 having a sulfation degree of from 3.5 to 4.

16. The N,O-oversulfated K5 polysaccharide of claim 15 having a sulfation degree of from 3.7 to 4.

17. The N,O-oversulfated K5 polysaccharide according to claim 14, having a molecular weight with a distribution from about 2,000 to about 16,000 Da.

18. The N,O-oversulfated K5 polysaccharide of claim 17, wherein said molecular weight distribution is from about 2,500 to about 10,000 Da with a mean molecular weight of about 6,500 Da.

19. The N,O-oversulfated K5 polysaccharide according to claim 14 having a molecular weight with a distribution from about 13,000 to about 65,000 Da.

20. The N,O-oversulfated K5 polysaccharide of claim 19, wherein said molecular weight distribution is from about 25,000 to about 50,000 Da with a mean molecular weight of about 40,000 Da.

21. The N,O-oversulfated K5 polysaccharide according to claim 14, having a molecular weight with a distribution from about 2,000 to about 65,000 Da with a mean molecular weight of 25,000–30,000 Da.

22. A N,O-oversulfated K5 polysaccharide according to claim 14 obtained by depolymerization having a mean molecular weight of from 2,000 to 5,000 Da.

23. A pharmaceutically acceptable salt of the N,O-oversulfated K5 polysaccharide of claim 14.

24. The salt of claim 23, selected from the group consisting of sodium, potassium, calcium, magnesium, aluminum and zinc salts.

25. N,O-oversulfated K5 polysaccharide constituted by a mixture of chains in which at least 90% of said chains have the formula

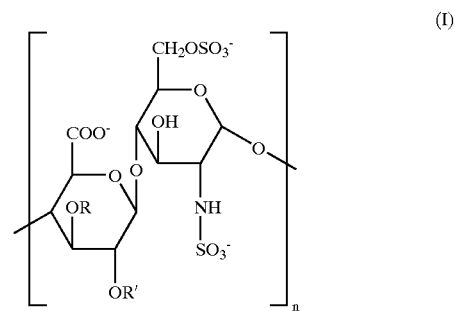

(I)

wherein n is from 3 to 100 and R and R' are hydrogen or a $SO_3^-$ group, at least one of R and R' being other than hydrogen, with the proviso that, in said Formula (I), R and R' are both $SO_3^-$ in from 60% to 100% of the n repeating disaccharide units and one of R and R' is hydrogen and the other is $SO_3^-$ in from 40% to 0% of the n repeating disaccharide units; the sulfation degree being from 3.2 to 4 and the corresponding cation being a chemically or pharmaceutically acceptable one.

26. The N,O-oversulfated K5 polysaccharide of claim 25 wherein said cation is selected from the group consisting of sodium, potassium, calcium, magnesium, aluminum and zinc ions.

27. A pharmaceutical or cosmetic composition comprising, as an active ingredient thereof, an active amount of a N,O-oversulfated K5 polysaccharide according to claim 14, in admixture with a pharmaceutical or cosmetic excipient or vehicle.

* * * * *